(12) United States Patent
Chang et al.

(10) Patent No.: US 11,819,358 B2
(45) Date of Patent: Nov. 21, 2023

(54) AUSCULTATION DEVICE AND AUSCULTATION METHOD USING AUSCULTATION DEVICE

(71) Applicant: Quanta Computer Inc., Taoyuan (TW)

(72) Inventors: Chia-Yuan Chang, Taoyuan (TW); Jung-Wen Chang, Taoyuan (TW); Chien-Hung Lin, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 679 days.

(21) Appl. No.: 17/000,772

(22) Filed: Aug. 24, 2020

(65) Prior Publication Data
US 2021/0353247 A1 Nov. 18, 2021

(30) Foreign Application Priority Data

May 14, 2020 (TW) .................................. 109115949

(51) Int. Cl.
*A61B 7/04* (2006.01)
*A61B 5/00* (2006.01)
(Continued)

(52) U.S. Cl.
CPC .............. *A61B 7/04* (2013.01); *A61B 5/0006* (2013.01); *A61B 5/318* (2021.01); *A61B 5/333* (2021.01);
(Continued)

(58) Field of Classification Search
None
See application file for complete search history.

(56) References Cited

U.S. PATENT DOCUMENTS

| 3,832,994 A * | 9/1974 | Bicher | A61B 5/349 128/903 |
| 4,446,873 A * | 5/1984 | Groch | A61B 5/352 600/528 |

(Continued)

FOREIGN PATENT DOCUMENTS

CN 104873186 A 9/2015

OTHER PUBLICATIONS

Machine translation of CN 104873186 (May 18, 2018), Claryvate Analytics (Year: 2023).*

(Continued)

*Primary Examiner* — Carl H Layno
*Assistant Examiner* — Manolis Pahakis
(74) *Attorney, Agent, or Firm* — McClure, Qualey & Rodack, LLP

(57) ABSTRACT

An auscultation device includes an electrocardiogram (ECG) device, a sound receiver device, a synchronization device and a processor. The ECG device is configured to receive an ECG signal. The sound receiver device is configured to receive a heart sound signal. The synchronization device is configured to transmit a synchronization signal to the ECG device and the sound receiver device, so that the ECG device starts to receive the ECG signal and the sound receiver device starts to receive the heart sound signal in time synchronization. Moreover, the processor is configured to generate an ECG according to the ECG signal, generate a heart sound diagram according to the heart sound signal, and generate a synchronization timing diagram according to the ECG and the heart sound diagram.

8 Claims, 10 Drawing Sheets

(51) Int. Cl.
  *A61B 5/333* (2021.01)
  *A61B 5/339* (2021.01)
  *A61B 5/352* (2021.01)
  *A61B 5/318* (2021.01)
  *A61B 5/363* (2021.01)

(52) U.S. Cl.
  CPC .............. *A61B 5/339* (2021.01); *A61B 5/352* (2021.01); *A61B 5/363* (2021.01); *A61B 5/683* (2013.01); *A61B 5/7282* (2013.01); *A61B 5/7285* (2013.01)

(56) References Cited

U.S. PATENT DOCUMENTS

| | | | | |
|---|---|---|---|---|
| 4,594,731 | A * | 6/1986 | Lewkowicz | A61B 7/04 600/528 |
| 5,862,803 | A * | 1/1999 | Besson | H03F 3/45103 128/903 |
| 6,600,949 | B1 * | 7/2003 | Turcott | A61B 5/0205 600/513 |
| 6,757,392 | B1 * | 6/2004 | Granzotto | A61B 5/742 600/509 |
| 7,177,686 | B1 * | 2/2007 | Turcott | A61N 1/36585 607/23 |
| 8,548,588 | B1 * | 10/2013 | Bauer | A61N 1/36578 607/18 |
| 9,492,138 | B2 * | 11/2016 | Kapoor | A61B 5/742 |
| 10,799,161 | B2 * | 10/2020 | von Luehmann | A61B 5/6814 |
| 10,828,007 | B1 * | 11/2020 | Telfort | A61B 5/6833 |
| 11,417,310 | B2 * | 8/2022 | Chang | G10K 11/341 |
| 11,633,158 | B2 * | 4/2023 | Wu | A61B 7/003 600/301 |
| 2003/0176800 | A1 | 9/2003 | Galen | A61B 7/04 600/528 |
| 2004/0215094 | A1 * | 10/2004 | Baumer | A61B 7/04 600/513 |
| 2004/0220487 | A1 * | 11/2004 | Vyshedskiy | A61B 5/24 600/528 |
| 2004/0260188 | A1 * | 12/2004 | Syed | A61B 7/04 600/509 |
| 2005/0124902 | A1 * | 6/2005 | Baumer | A61B 7/04 600/509 |
| 2006/0155202 | A1 * | 7/2006 | Arand | A61B 5/742 600/528 |
| 2007/0032728 | A1 * | 2/2007 | Longhini | A61B 5/021 600/513 |
| 2007/0219059 | A1 * | 9/2007 | Schwartz | A61B 5/02405 482/8 |
| 2008/0027333 | A1 * | 1/2008 | Peretto | A61B 7/04 600/513 |
| 2008/0294213 | A1 * | 11/2008 | Holmstrom | A61N 1/36843 607/19 |
| 2009/0062665 | A1 * | 3/2009 | Peretto | A61B 5/021 600/485 |
| 2009/0254139 | A1 * | 10/2009 | Bjorling | A61B 7/04 607/17 |
| 2010/0087746 | A1 * | 4/2010 | Radzievsky | A61B 7/003 708/271 |
| 2010/0249629 | A1 * | 9/2010 | Schmidt | A61B 7/04 600/528 |
| 2011/0257548 | A1 * | 10/2011 | Dong | A61B 7/04 600/528 |
| 2011/0275909 | A1 * | 11/2011 | Kim | A61B 5/02007 600/301 |
| 2013/0116584 | A1 * | 5/2013 | Kapoor | A61B 5/282 600/513 |
| 2013/0137997 | A1 * | 5/2013 | Patangay | A61B 5/02028 600/513 |
| 2014/0073980 | A1 * | 3/2014 | Scheiner | A61B 7/04 600/513 |
| 2015/0057512 | A1 * | 2/2015 | Kapoor | A61B 5/02405 600/513 |
| 2015/0065814 | A1 * | 3/2015 | Kapoor | A61B 8/00 600/513 |
| 2015/0257647 | A1 * | 9/2015 | Buck | A61B 5/6804 600/509 |
| 2016/0066808 | A1 * | 3/2016 | Hijazi | A61B 5/333 600/382 |
| 2016/0100817 | A1 * | 4/2016 | Hussain | A61B 7/04 600/528 |
| 2016/0151037 | A1 * | 6/2016 | Lin | A61B 7/04 600/513 |
| 2017/0119255 | A1 * | 5/2017 | Mahajan | A61B 5/1135 |
| 2017/0150891 | A1 * | 6/2017 | Tsuchimoto | A61B 5/02416 |
| 2017/0185737 | A1 * | 6/2017 | Kovacs | A61B 5/02416 |
| 2018/0116593 | A1 * | 5/2018 | An | A61N 1/3684 |
| 2018/0192965 | A1 * | 7/2018 | Rose | G16H 80/00 |
| 2018/0317789 | A1 * | 11/2018 | Ransbury | G16H 40/67 |
| 2019/0046053 | A1 * | 2/2019 | Jiang | A61B 5/7225 |
| 2019/0059748 | A1 * | 2/2019 | Kaiser | A61B 7/026 |
| 2019/0105019 | A1 * | 4/2019 | Pagoulatos | A61B 8/5284 |
| 2019/0183454 | A1 * | 6/2019 | Kjær Thing Riknagel | A61B 8/02 |
| 2019/0209028 | A1 * | 7/2019 | Baxi | A61B 5/25 |
| 2020/0163575 | A1 * | 5/2020 | Samuelsson | A61B 5/6801 |
| 2020/0245889 | A1 * | 8/2020 | Telenkov | A61B 5/316 |
| 2021/0321949 | A1 * | 10/2021 | Wu | A61B 5/725 |
| 2021/0353247 | A1 * | 11/2021 | Chang | A61B 5/352 |
| 2021/0358472 | A1 * | 11/2021 | Chang | G10K 11/341 |
| 2022/0175254 | A1 * | 6/2022 | Hui | H04W 4/38 |

OTHER PUBLICATIONS

Chinese language office action dated Oct. 15, 2020, issued in application No. TW 109115949.

* cited by examiner

| | inhalation | exhalation |
|---|---|---|
| C1 — physiological split sound | —  == <br> S1  S2 | —  — <br> S1  S2 |
| C2 — pulmonary hypertension, mitral valve reflux, and right bundle branch block | —  == <br> S1  S2 | —  == <br> S1  S2 |
| C3 — diaphragm defect in the ventricle and right ventricular failure | —  == <br> S1  S2 | —  == <br> S1  S2 |

FIG. 7

AUSCULTATION DEVICE AND AUSCULTATION METHOD USING AUSCULTATION DEVICE

CROSS REFERENCE TO RELATED APPLICATIONS

This Application claims priority of Taiwan Patent Application No. 109115949, filed on May 14, 2020 the entirety of which is incorporated by reference herein.

BACKGROUND OF THE INVENTION

Field of the Invention

The present disclosure relates to an auscultation device and auscultation method using the auscultation device and, in particular, to an auscultation device and an auscultation method using the auscultation device to generate a synchronization timing diagram based on an electrocardiogram and a heart sound image.

Description of the Related Art

The effective use of traditional stethoscopes depends mainly on the doctor's hearing, so it depends on the doctor's experience and ability to make a correct determination. An electronic stethoscope converts analog heart sounds into digital heart sounds, which is convenient for recording via electronic device, and which is convenient for subsequent record-tracking and signal-processing. However, in the diagnostic procedures employed by traditional medical institutions and health examinations, the measurement of the heart sound signal and the electrocardiogram (ECG) signal are measured separately, which is not only complicated, but requires different measurement devices.

Therefore, how to measure the heart sound signal and the ECG signal more conveniently has become one of the problems to be solved in the field.

BRIEF SUMMARY OF THE INVENTION

In accordance with one feature of the present invention, the present disclosure provides an auscultation device. The auscultation device includes an electrocardiogram (ECG) device, a sound receiver device, a synchronization device and a processor. The ECG device is configured to receive an ECG signal. The sound receiver device is configured to receive a heart sound signal. The synchronization device is configured to transmit a synchronization signal to the ECG device and the sound receiver device, so that the ECG device starts to receive the ECG signal and the sound receiver device starts to receive the heart sound signal in time synchronization. Moreover, the processor is configured to generate an ECG according to the ECG signal, generate a heart sound diagram according to the heart sound signal, and generate a synchronization timing diagram according to the ECG and the heart sound diagram.

In accordance with one feature of the present invention, the present disclosure provides an auscultation method. The auscultation method includes: transmitting a synchronization signal to trigger an ECG device to start receiving the ECG signal and trigger a sound receiver device to start receiving a heart sound signal in time synchronization; and generating an ECG according to the ECG signal, generating a heart sound diagram according to the heart sound signal, and generating a synchronization timing diagram according to the ECG and the heart sound diagram.

Based on the information described above, it is possible to simultaneously measure the ECG signal and the heart sound signal, and generate a synchronization timing diagram of the combined ECG signal and heart sound signal using the auscultation device and the auscultation method using the auscultation device. In addition, the synchronization device can synchronize the time when the ECG device starts to receive the ECG signal and the sound receiver device starts to receive the heart sound signal, so that the ECG device and the sound receiver device can readjust the timing and receive the signal at the same time. The starting point and time axis of the generated synchronization timing diagram are consistent. The comparison of the heart sound signal and the ECG signal is also more accurate. The synchronization timing diagram can be transmitted to the mobile phone or computer through a wired or wireless transmission. Moreover, the synchronization timing diagram can provide reference information for waveform analysis for the doctor to reference.

BRIEF DESCRIPTION OF THE DRAWINGS

In order to describe the manner in which the above-recited and other advantages and features of the disclosure can be obtained, a more particular description of the principles briefly described above will be rendered by reference to specific examples thereof which are illustrated in the appended drawings. Understanding that these drawings depict only example aspects of the disclosure and are not therefore to be considered to be limiting of its scope, the principles herein are described and explained with additional specificity and detail through the use of the accompanying drawings in which:

FIG. 7 is a schematic diagram of an analyzing measurement results method 700 in accordance with one embodiment of the present disclosure.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The present invention will be described with respect to particular embodiments and with reference to certain drawings, but the invention is not limited thereto and is only limited by the claims. It will be further understood that the terms "comprises," "comprising," "comprises" and/or "including," when used herein, specify the presence of stated features, integers, steps, operations, elements, and/or components, but do not preclude the presence or addition of one or more other features, integers, steps, operations, elements, components, and/or groups thereof.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Figure 1A:
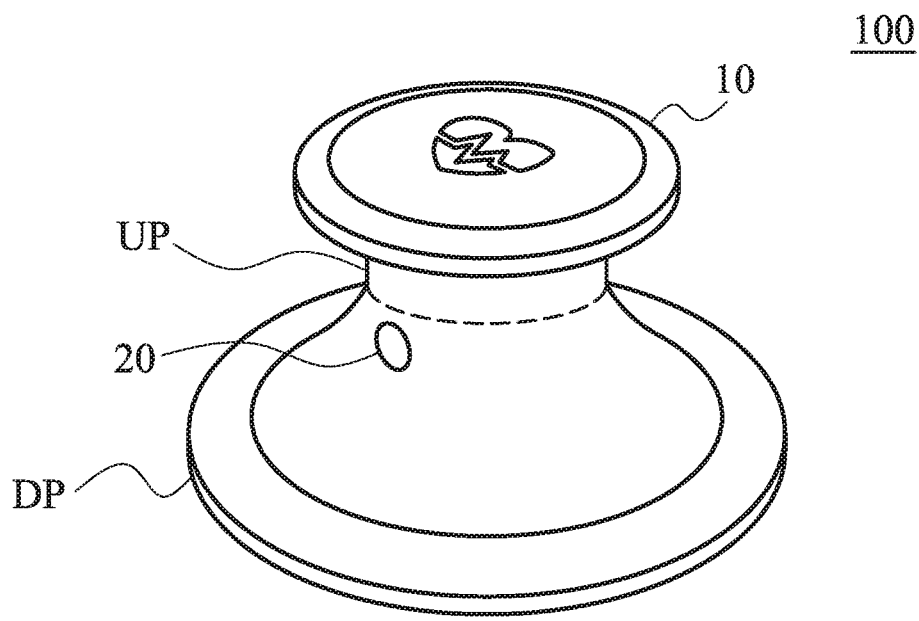
FIG. 1A is a top view of an auscultation device in accordance with one embodiment of the present disclosure.
Figure 1B:
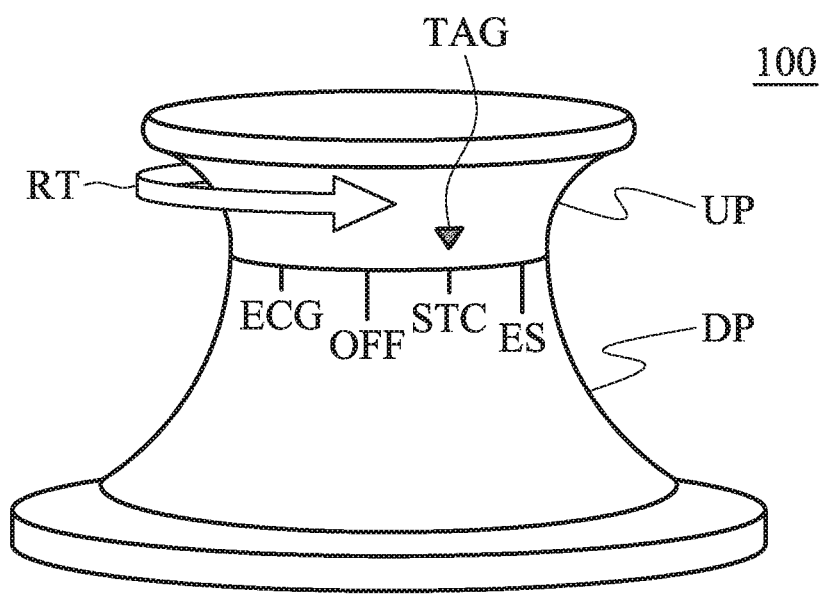
FIG. 1B is a side view of an auscultation device in accordance with one embodiment of the present disclosure.
Figure 1C:
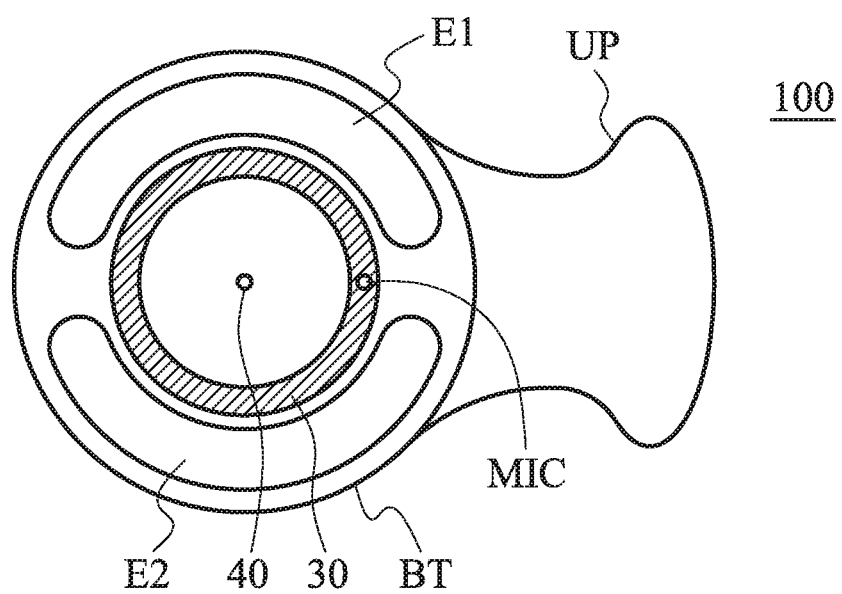
FIG. 1C is a bottom view of an auscultation device in accordance with one embodiment of the present disclosure.

Please refer to FIGS. 1A-1C, FIG. 1A is a top view of an auscultation device 100 in accordance with one embodiment of the present disclosure. FIG. 1B is a side view of an auscultation device 100 in accordance with one embodiment of the present disclosure. FIG. 1C is a bottom view of an auscultation device 100 in accordance with one embodiment of the present disclosure.

In one embodiment, the auscultation device 100 includes an electrocardiogram (ECG) device, a sound receiver device, a synchronization device and a processor. The ECG device, sound receiver device, synchronization device and processor can be placed in the upper part UP or lower part DP of the auscultation device 100, for example, all the components are placed in the lower part DP of the auscultation device 100. The ECG device is electrically coupled to the processor. The sound receiver device is electrically coupled to the processor. Moreover, the synchronization device is electrically coupled to the electrocardiogram device and the sound receiver device. In one embodiment, the auscultation device 100 includes an analog-to-digital device for converting the received analog signal about physiology into a digital signal. The placement method of these devices is not limited thereto.

As shown in FIG. 1A, the auscultation device 100 is divided into an upper part UP and a lower part DP, and the upper part UP and the lower part DP are electrically coupled. In one embodiment, a display 10 is provided on the upper part UP of the auscultation device 100 and not contact the skin surface. The display 10 is configured to display a measurement state, such as a normal or abnormal state of an ECG signal. The earphone jack 20 may be provided in the upper part UP or lower part DP of the auscultation device 100. When the earphone is inserted into the earphone jack 20, the heart sound signal (i.e., heartbeat) received by the sound receiver device can be heard. In one embodiment, the user can insert the earphone into the earphone jack 20 to hear the heart sound signal immediately. In one embodiment, the auscultation device 100 can record the ECG signal received by the ECG device and the heart sound signal received by the sound receiver device, and store these signal in a storage device, such as the internal storage space of the auscultation device 100, or the auscultation device 100 transmits these signals to the storage space of external mobile phones, tablets, computers, and other electronic devices for storage via wired/wireless methods. After the user inserts the earphone into the earphone jack 20, these signals can be taken out from the storage space and played or displayed by the auscultation device 100.

As shown in FIG. 1B, from the side view of the auscultation device 100, the upper part UP of the auscultation device 100 can be rotated through the rotation mechanism (for example, the upper part UP is rotated from left to right in the direction RT) to align a mark TAG with a measurement mode (such as an ECG measurement mode, an ECG, an OFF mode, a heart sound measurement mode STC, or a synchronous measurement mode ES) of the lower part DP of the auscultation device 100 to select one of the measurement modes. For example, the user may rotate the mark TAG on the upper part UP of the auscultation device 100 to be aligned with the position of the ECG mark, entering the ECG measurement mode to select the auscultation device 100 to measure the ECG signal. Among them, the synchronous measurement mode ES refers to measuring the ECG signal and the heart sound signal at the same time.

As shown in FIG. 1C, as can be seen from the bottom view of the auscultation device 100, the auscultation device 100 includes a plurality of electrode patches E1, E2, respectively (with an distance between the two electrode patches E1 and E2) located on the bottom BT of the auscultation device 100. The bottom BT of the auscultation device 100 is configured to form contact with the skin surface to receive the ECG signal. The electrode patches E1 and E2 belong to a part of the ECG device and receive the ECG signal through contact with the skin. The bottom BT of the auscultation device 100 includes a ring-shaped component 30 where the microphone MIC can be disposed. In one embodiment, the microphone MIC belongs to a part of the sound receiver device, and is disposed at the bottom BT of the auscultation device 100 for receiving heart sound signals. In one embodiment, the microphone MIC may also be disposed in the center 40 of the bottom BT of the auscultation device 100. However, the position of the microphone MIC is not limited thereto, and the microphone MIC can be placed at a position with better sound receiving according to the actual implementation.

Figure 2:
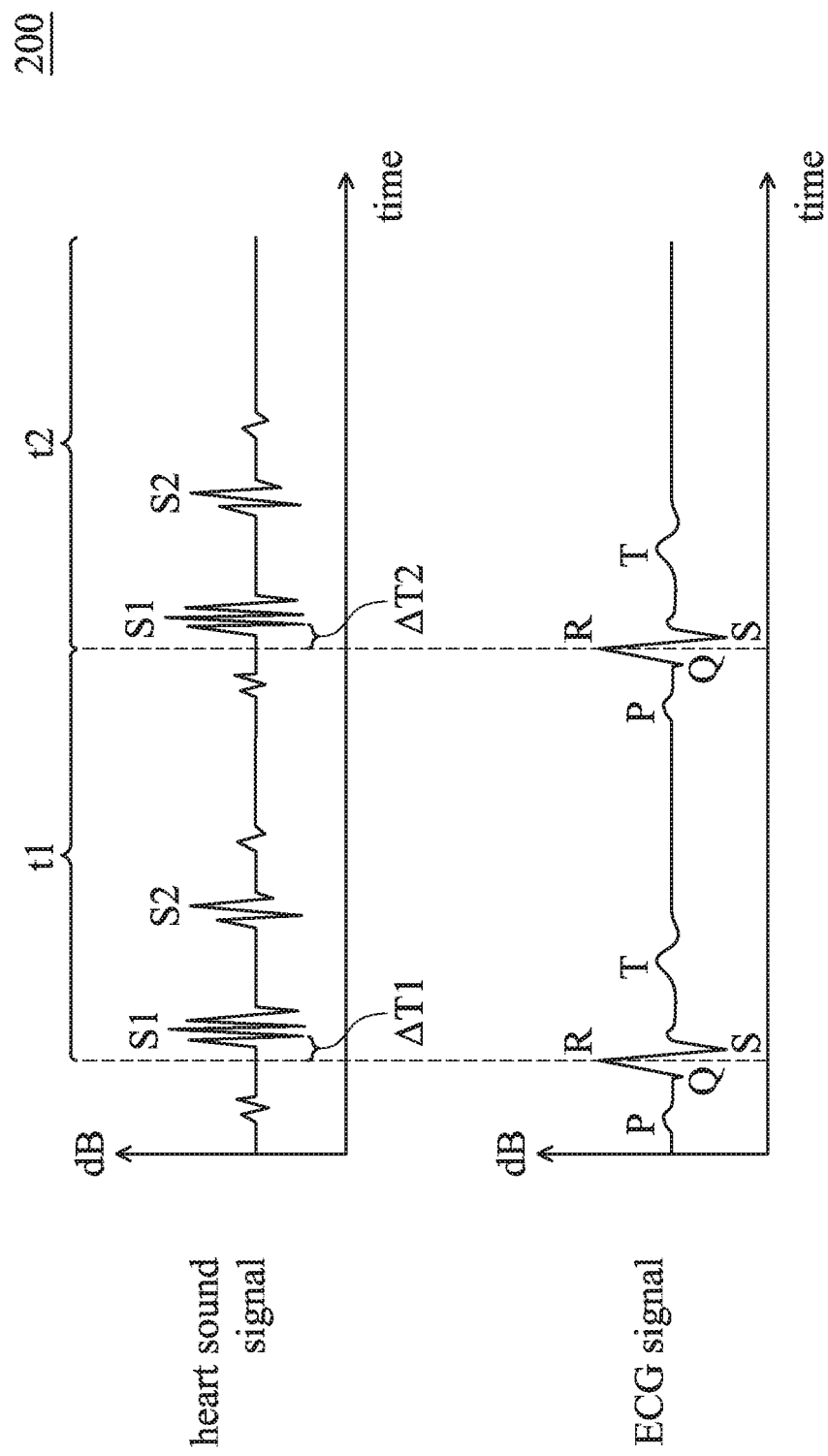
FIG. 2 is a schematic diagram of a synchronization timing diagram in accordance with one embodiment of the present disclosure.
Figure 3:
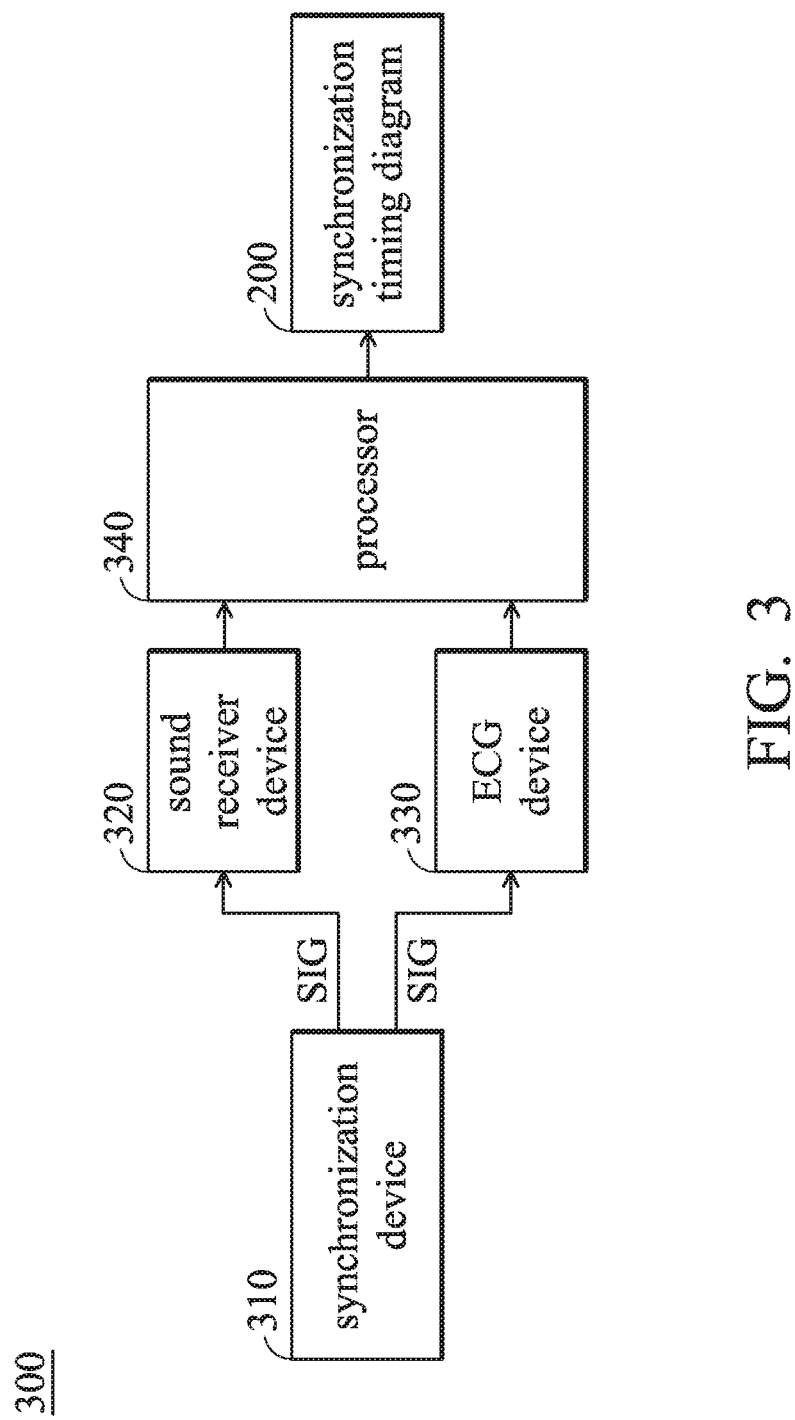
FIG. 3 is a schematic diagram of a synchronization timing method in accordance with one embodiment of the present disclosure.
Figure 4:
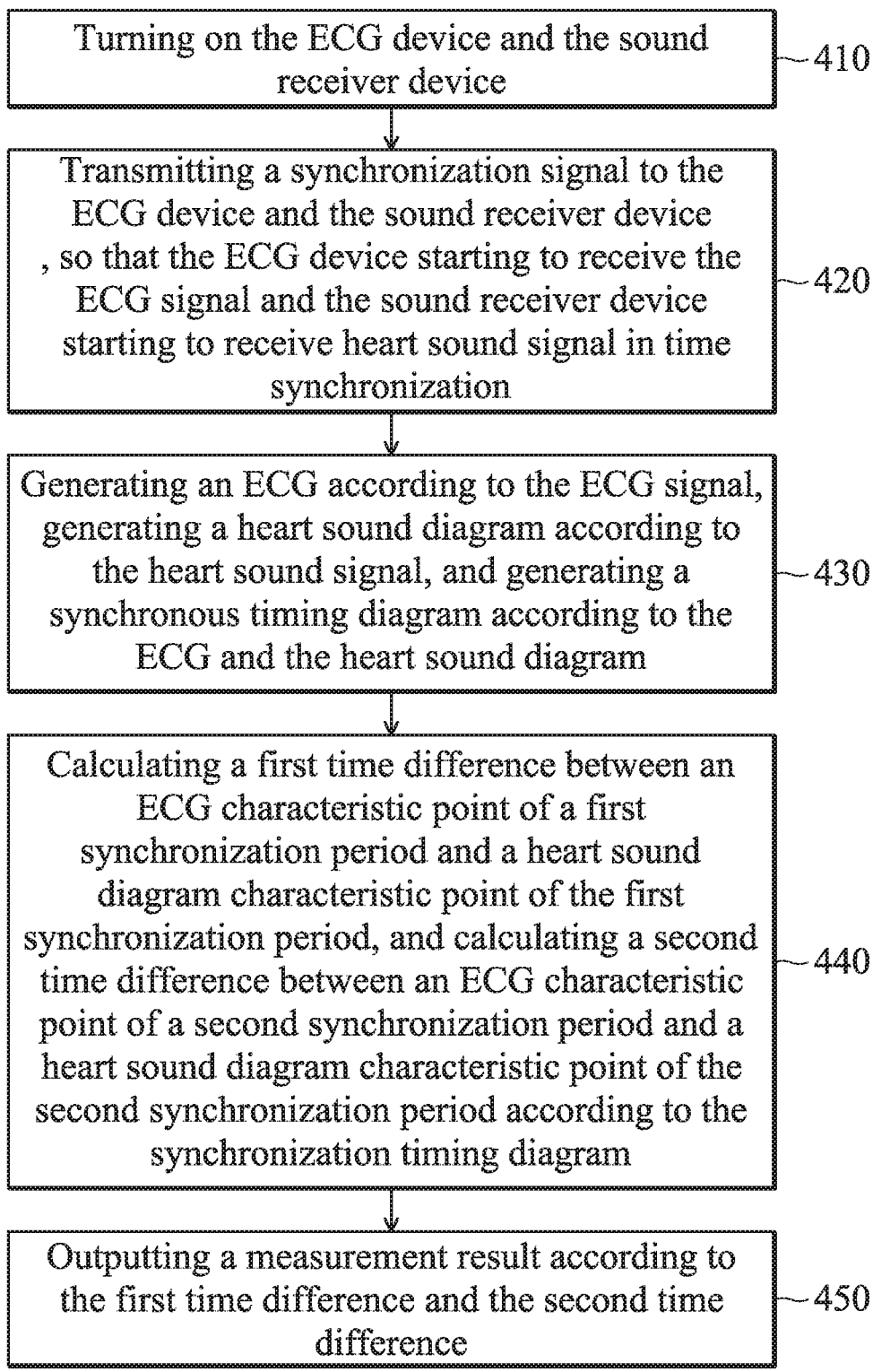
FIG. 4 is a flowchart of an auscultation method using an auscultation device according to an embodiment of the invention.

Please refer to FIGS. 2-4. FIG. 2 is a schematic diagram of a synchronization timing diagram 200 in accordance with one embodiment of the present disclosure. FIG. 3 is a schematic diagram of a synchronization timing method 300 in accordance with one embodiment of the present disclosure. FIG. 4 is a flowchart of an auscultation method 400 using an auscultation device according to an embodiment of the invention.

In step 410, the synchronous measurement mode ES is selected for turning on the ECG device 330 and the sound receiver device 320.

In one embodiment, the preset mode activated by the auscultation device 100 can be set as the synchronous measurement mode ES. In one embodiment, when the mark TAG of the upper part UP of the auscultation device 100 rotates to be aligned with the position of the synchronized measurement mode ES, the auscultation device 100 turns on or enters the synchronized measurement mode ES.

In one embodiment, when the electrode patches E1, E2 of the auscultation device 100 contact the human body over a time threshold (for example, 2 seconds), the auscultation device 100 automatically turns on the synchronous measurement mode ES.

In step 420, the synchronization device 310 transmits a synchronization signal SIG to the ECG device 330 and the sound receiver device 320, so that the ECG device 330 starts to receive the ECG signal and the sound receiver device 320 starts to receive heart sound signal in time synchronization.

In one embodiment, the synchronization device 310 can be a high-frequency quartz oscillator, which can simultaneously send a pulse signal SIG to the sound receiver device 320 and the ECG device 330. In this way, the sound receiver device 320 and the ECG device 330 can start to receive the respective signals simultaneously (the ECG device 330 starts to receive the ECG signal and the sound receiver device 320 starts to receive the heart sound signal), so that the two devices can be aligned at the timing of starting the measurement. For example, the state of the heart sound signal and the ECG signal at this point can be known at the f start of measurement or at the same time, thus to reduce the inconsistency in the timing.

In step 430, the processor 340 is used to generate an ECG according to the ECG signal, generate a heart sound diagram according to the heart sound signal, and generate a synchronous timing diagram 200 according to the ECG and the heart sound diagram.

In one embodiment, the processor 340 measures ECG signals for a certain period of time (for example, 10 seconds) for generating an ECG, in the same time, the heart sound signals are simultaneously measured for generating a heart sound diagram. Then the ECG and the heart sound diagram are combined and drawn in the same diagram to produce a synchronization timing diagram 200, as shown in FIG. 2, for example, to facilitate the medical clinic to determine the ECG signal and heart sound signal at the same time.

In one embodiment, the synchronization timing diagram 200 can be stored in the storage space internal of the auscultation device 100, or the auscultation device 100 can transmit these signals to the external storage space of mobile phone, tablet, computer, etc. via wired/wireless method.

Figure 8:
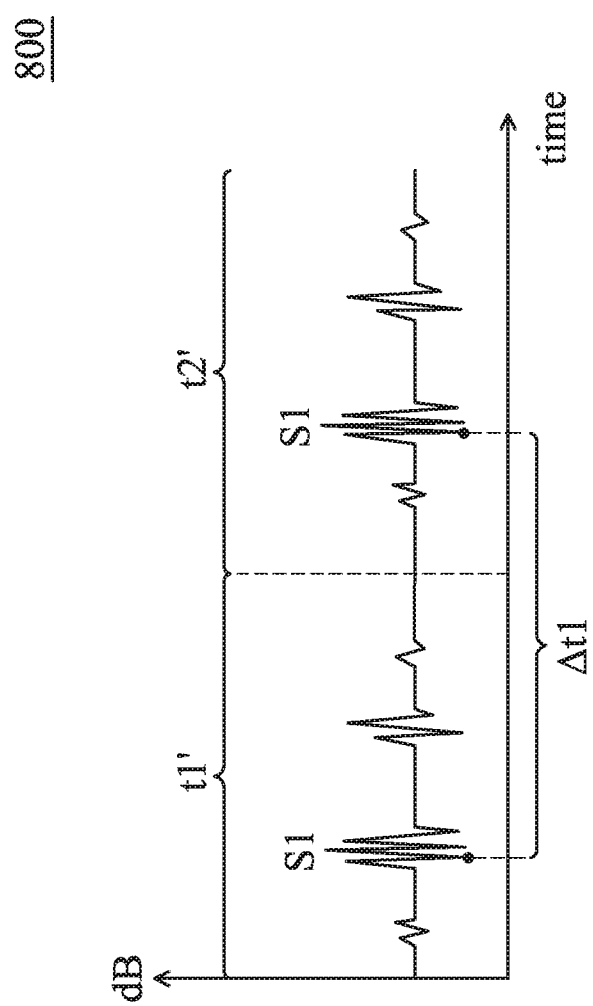
FIG. 8 is a schematic diagram of a heartbeat cycle in accordance with one embodiment of the present disclosure.
Figure 9:
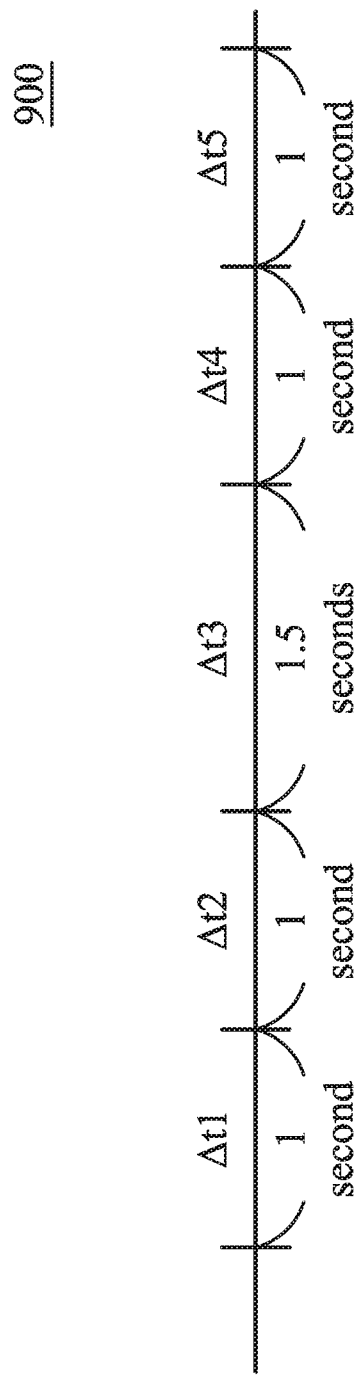
FIG. 9 is a schematic diagram of a heartbeat cycle analyzing method in accordance with one embodiment of the present disclosure.

In step 440, the processor 340 calculates a first time difference $\Delta T1$ between an ECG characteristic point (for example, R wave peak value) of a first synchronization period t1 and a heart sound diagram characteristic point (for example, the first trough of the first heart sound S1) of the first synchronization period t1, and calculates a second time difference $\Delta T2$ between an ECG characteristic point (for example, R wave peak value) of a second synchronization period t2 and a heart sound diagram characteristic point (for example, the first trough of the first heart sound S1) of the second synchronization period t2 according to the synchronization timing diagram 200 (detailed descriptions of FIG. 8 and FIG. 9 below). In one embodiment, the waveforms P, Q, R, S, and T in the ECG can also be used as ECG characteristic points.

The definitions of the respective ECG characteristic points and the heart sound diagram characteristic points in the first synchronization period t1 and the second synchronization period t2 should be consistent or the same. For example, if the ECG characteristic point of the first synchronization period t1 is defined as the S wave valley value, the ECG characteristic point of the second synchronization period t2 should also be defined as the S wave valley value. If the heart sound diagram characteristic point of the first synchronization period t1 is defined as the first peak of the second heart sound S2, the heart sound diagram characteristic point of the second synchronization period t2 should also be defined as the first peak of the second heart sound S2.

In step 450, the processor 340 outputs a measurement result according to the first time difference $\Delta T1$ and the second time difference $\Delta T2$.

In an embodiment, when the processor 340 determines that a time difference or time gap between the first time difference $\Delta T1$ and the second time difference $\Delta T2$ is greater than a time threshold, the processor 340 determines that the measurement result is abnormal. When the processor 340 determines that the time difference or time gap between the first time difference $\Delta T1$ and the second time difference $\Delta T2$ is not greater than a time threshold, the processor 340 determines that the measurement result is normal.

Figure 5:
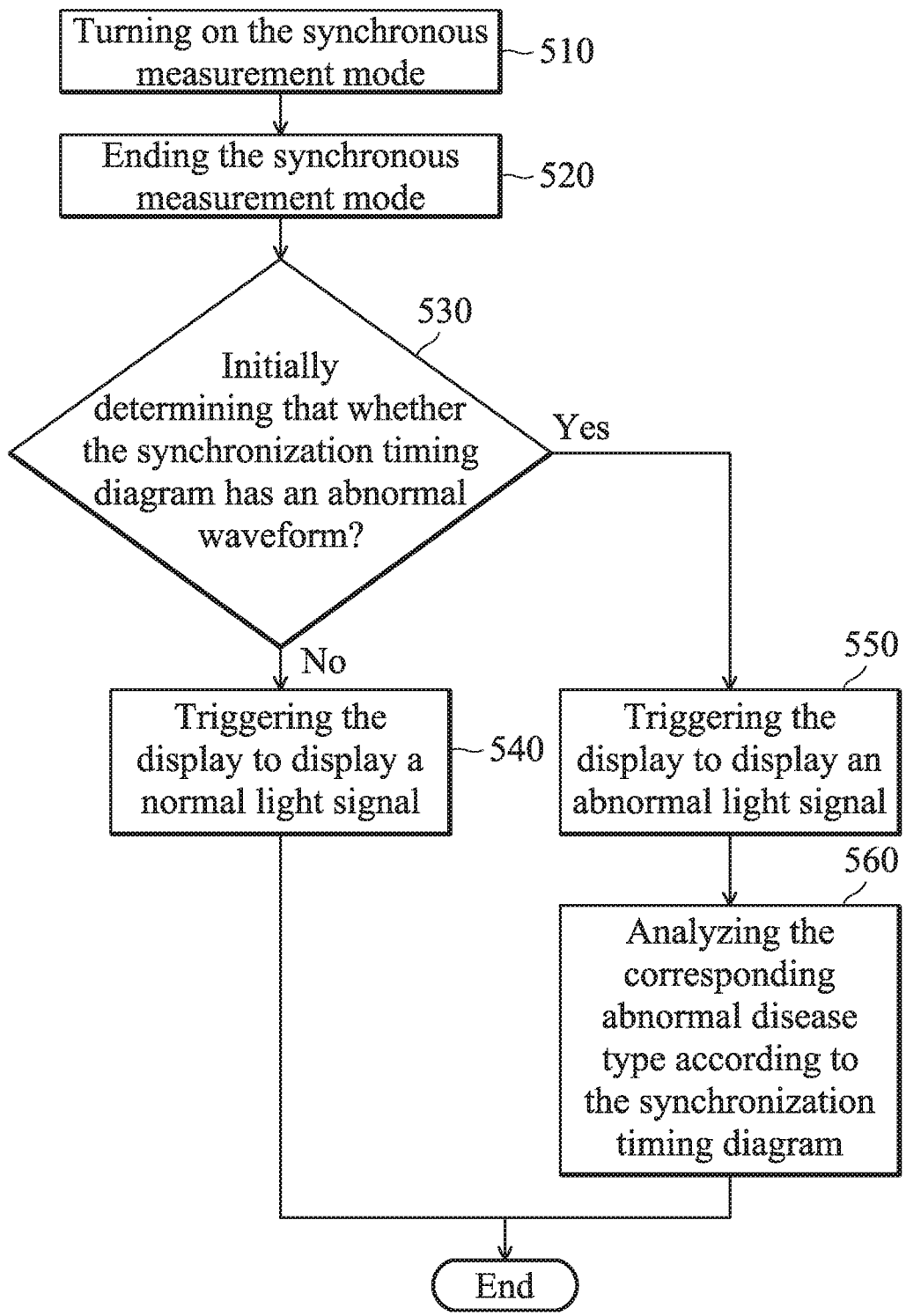
FIG. 5 is a flowchart of a waveform analysis method 500 in accordance with one embodiment of the present disclosure.
Figure 6:
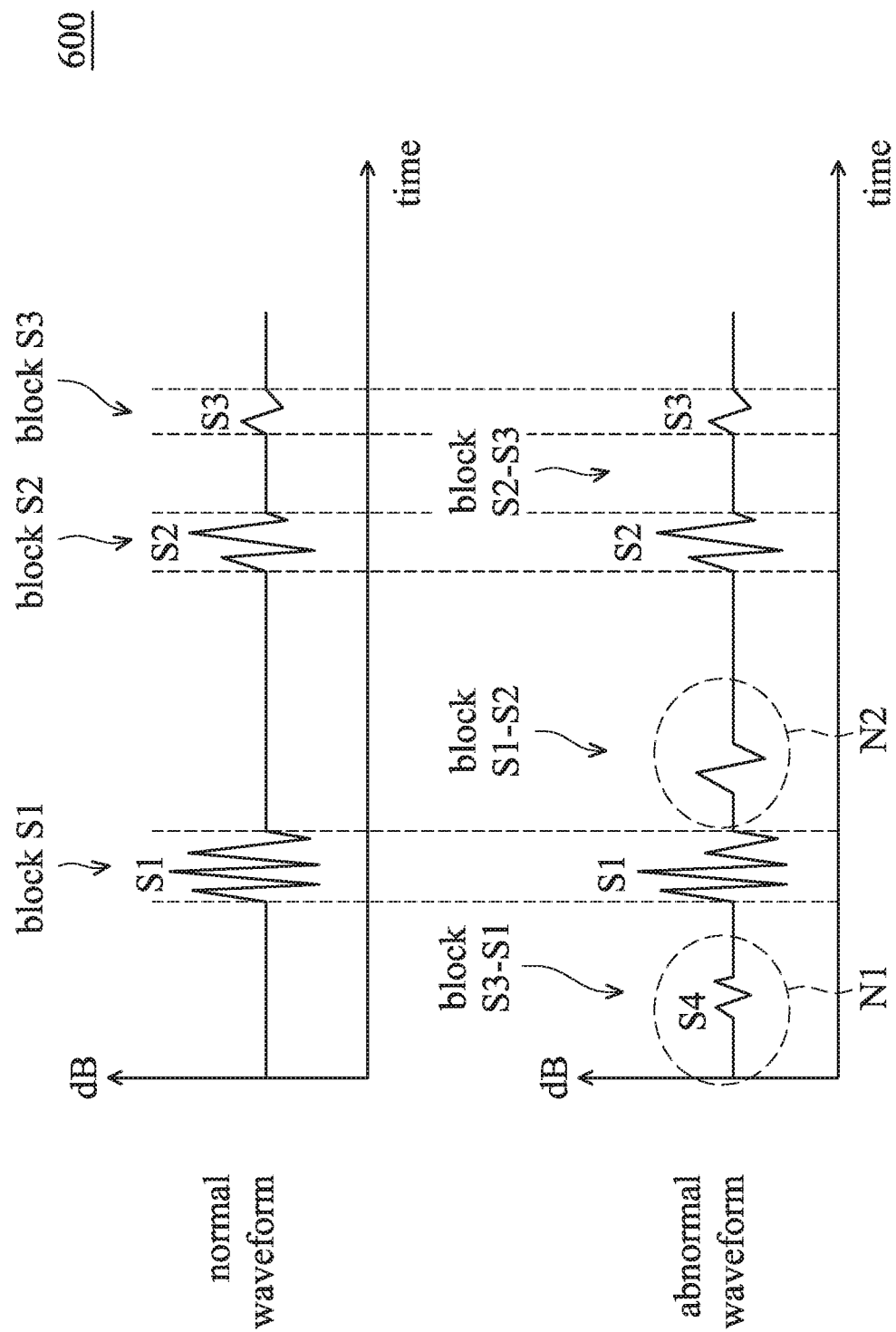
FIG. 6 is a heart sound diagram illustrating an analyzing measurement results of a method in accordance with one embodiment of the present disclosure.

FIG. 5 is a flowchart of a waveform analysis method 500 in accordance with one embodiment of the present disclosure. FIG. 6 is a heart sound diagram 600 illustrating an analyzing measurement results method in accordance with one embodiment of the present disclosure. FIG. 7 is a schematic diagram of an analyzing measurement results method 700 in accordance with one embodiment of the present disclosure.

In step 510, the auscultation device 100 turns on the synchronous measurement mode ES.

In one embodiment, when the mark TAG of the upper part UP of the auscultation device 100 rotates to be aligned with the position of the synchronized measurement mode ES, the auscultation device 100 turns on the synchronized measurement mode ES.

In one embodiment, when the electrode patches E1, E2 of the auscultation device 100 contact the human body over a time threshold (for example, 2 seconds), the auscultation device 100 automatically turns on the synchronous measurement mode ES.

In step 520, the auscultation device 100 ends the synchronous measurement mode ES.

In one embodiment, when performing the synchronous measurement mode ES, the auscultation device 100 measures the ECG signals for a certain period of time (for example, 10 seconds) to generate an ECG. During this period, the heart sound signals are measured simultaneously and a heart sound diagram is generated. The ECG and the heart sound diagram are combined and drawn in the same diagram to generate a synchronization timing diagram (e.g., a synchronization timing diagram 200), and the synchronization timing diagram 200 is stored.

In step 530, the processor 340 initially determines that whether the synchronization timing diagram (for example, the synchronization timing diagram 200) has an abnormal waveform. If the processor 340 initially determines that the synchronization timing diagram 200 has an abnormal waveform, the step 550 is performed. If the processor 340 initially determines that the synchronization timing diagram 200 has no abnormal waveform, the step 540 is performed.

It should be noted that the actions of steps 510-530 are equivalent to the flowchart in FIG. 4.

In one embodiment, when the processor 340 determines that the heart sound signal has a noise in a plurality of flat areas, a split sound in a first heart sound S1, a split sound in a second heart sound S2, a plurality of heartbeat cycles are irregular or the time difference of these heartbeat cycles is greater than the time threshold according to the synchronization timing diagram (for example, the synchronization timing diagram 200), the processor 340 determines that the measurement result is abnormal.

In an embodiment, please refer to the heart sound diagram 600 in FIG. 6. In the normal waveforms, only the block S1, block S2, and block S3 have waveforms. The waveform of the block S1 represents the first heart sound S1. The waveform of block S2 represents the second heart sound S2. Moreover, the waveform of block S3 represents the third heart sound S3. In other words, the areas between the current block S3 and the next block S1, the area between block S1 and block S2, and the area between block S2 and block S3 are flat areas in the normal waveforms.

In addition, in practice, there may be a fourth heart sound S4 in the heart sound waveform. However, the fourth heart sound S4 is usually caused by high atrial pressure and ventricular hypertrophy. It occurs before the first heart sound S1 and is rarely heard by normal people. Therefore, in the normal waveform, except for the S1 block, the S2 block, and the S3 block, the other parts should be flat areas.

The abnormal waveform shows that blocks N1 and N2 are abnormal. These two places should be flat areas in the normal waveform, but the waveform appears in the abnormal waveform. Therefore, the processor 340 determines that the measurement result is abnormal.

In step 530, the heart sound waveform can be further split into a few large blocks and compared with the normal waveform to determine whether the heart sound waveform is normal or abnormal, and to increase determination speed. Detailed waveform analysis is performed in step 560.

In step 540, the processor 340 triggers the display 10 to display a normal light signal. This indicates that the measurement status is normal.

In step 550, the processor 340 triggers the display 10 to display an abnormal light signal. This indicates that the measurement status is abnormal.

In step 560, the processor 340 analyzes the corresponding abnormal disease type according to the synchronization timing diagram (for example, the synchronization timing diagram 200).

In one embodiment, when the processor 340 determines via analysis that a split sound exists in the first heart sound S1 or a split sound exists in the second heart sound S2, the processor 340 further determines the heart sound splitting status by analyzing the inhalation volume and the exhalation volume according to the split sound of the first heart sound S1 and the split sound of the second heart sound S2, a time difference between the first heart sound S1 and the second heart sound S2, or whether a noise exists between the first heart sound S1 and the second heart sound S2.

Please refer to FIG. 7, the straight line in the figure represents the volume, and here the partial volume of the S1 block and the S2 block is taken (for example, a part greater than a volume threshold is taken as a representative). Please look at column C1 firstly. When inhaling, the volume of the block S1 is normal (a straight line, there is no split sound, not too long (when the straight line is too long representing the heart sound is too loud), not too short (when the straight line is too short representing the heart sound volume is low), and no special long sound, then it is regarded as normal). When inhaling, the volume of the block S2 appears long and short, indicating that there is a split sound in the second heart sound S2. Moreover, when exhaling, the volume of the block S1 is normal, and the volume of the block S2 is also normal, but the delay of the block S2 is too long (the thicker line indicates delay), so it is not normal. When the heart sound signal in this form is analyzed according to the measurement result, the processor 340 determines that there is a physiological split sound in the measurement result.

In column C2, the volume of the block S1 appears one length and one short when inhaling, indicating that there is a split sound in the first heart sound S1. When inhaling, there are two long straight lines in the volume of the block S2, indicating that there is a split sound in the second heart sound S2. There is a long and a short in the block S1 when exhaling, which means that there is a split sound in the first heart sound S1. Moreover, two lines that are too close to the volume of the block S2 during exhalation, it means causing a split sound in a short time, so it is not normal. When the measurement result analyzes the heart sound signal of this type, the processor 340 determines that the measurement result has a high probability of problems such as pulmonary hypertension, mitral valve reflux, and right bundle branch block.

In column C3, the volume of the block S1 when inhaling is normal. The volume of the block S2 when inhaling appears two long straight lines, indicating that there is a split sound in the second heart sound S2. The volume of the block S1 when exhaling is normal. There are two long straight lines in the volume of the block S2 during exhalation, which means that the second heart sound S2 has a split sound, so it is abnormal. When the measurement result analyzes the heart sound signal of this type, the processor 340 determines that the measurement result has a higher probability of problems such as diaphragm defect in the ventricle and right ventricular failure.

In one embodiment, the processor 340 can select the abnormal waveform segment and compare it with the symptom database to summarize the possible symptom types with a probability value (for example, comparing the abnormal waveform segment with the multiple symptom waveforms stored in the symptom database, and each comparison produce a similarity percentage).

FIG. 8 is a schematic diagram of a heartbeat cycle 800 in accordance with one embodiment of the present disclosure. FIG. 9 is a schematic diagram of a heartbeat cycle analyzing method 900 in accordance with one embodiment of the present disclosure.

In one embodiment, the processor 340 calculates a first cycle time difference $\Delta t1$ between the first heart sound S1 of a first heart sound cycle t1' and the first heart sound S1 of a second heart sound cycle t2', calculates a second cycle time difference $\Delta t2$ between the first heart sound S1 of the second heart sound cycle t2' and the first heart sound S1 of a third heart sound cycle, calculates a third cycle time difference $\Delta t3$ between the first heart sound S1 of the third heart sound cycle and the first heart sound S1 of a fourth heart sound cycle, an average cycle time difference is calculated based on the first cycle time difference $\Delta t1$, the second cycle time difference $\Delta t2$ and the third cycle time difference $\Delta t3$, and then subtracts the smallest one from the largest one of the first cycle time difference, the second cycle time difference and the third heart sound time, so as to obtain a first value, and the first value is divided by an average heartbeat to obtain a second value, when the second value is greater than a heartbeat threshold, the processor 340 determines that the heartbeat cycles are irregular.

In one embodiment, the heartbeat threshold may be one-sixth of the average heartbeat.

In FIG. 8, the processor 340 captures the occurrence time of the trough (as a characteristic point) of the first heart sound S1 of the first heart sound cycle t1' and the occurrence time of the trough of the first heart sound S1 of the second heart sound cycle t2', calculates the first cycle time difference $\Delta t1$ between the two first heart sounds S1. The processor 340 can calculate other cycle time differences after the second heart sound cycle t2' in the same way. In other words, the processor 340 calculates the time difference between feature points between two adjacent cycles. However, the location of the feature points in this case is not limited to the trough, as long as the location of the feature points are the same for each heart sound cycle. For example, the feature points can be defined as the peak time of the first heart sound S1 and the second heart sound S2, or the feature points also can be defined as the trough time of the first heart sound S1 and the second heart sound S2, etc.

In one embodiment, as shown in FIG. 9, the first cycle time difference Δt1 is 1 second, the second cycle time difference Δt2 is 1 second, the third cycle time difference Δt3 is 1.5 seconds, and the fourth cycle time difference Δt4 is 1 second, and the difference of the fifth cycle time Δt5 is 1 second. The processor 340 averages these time difference to obtain an average cycle time difference of 1.1 seconds, and then subtracts the smallest one of the cycle time differences of 1 from the largest one of the cycle time differences of 1.5 to obtain a first value of 0.5, and then the first value 0.5 is divided by the average heartbeat to obtain a second value. When the second value is greater than the heartbeat threshold, the processor 340 determines that these heartbeat cycles are irregular.

Based on the information described above, with the auscultation device and the auscultation method using the auscultation device, it is possible to simultaneously measure the ECG signal and the heart sound signal, and generate a synchronization timing diagram of the combined ECG signal and heart sound signal. In addition, the synchronization device can synchronize the time when the ECG device starts to receive the ECG signal and the sound receiver device starts to receive the heart sound signal, so that the ECG device and the sound receiver device can readjust the timing and receive the signal at the same time. The starting point and time axis of the generated synchronization timing diagram are consistent. The comparison of the heart sound signal and the ECG signal is also more accurate. The synchronization timing diagram can be transmitted to the mobile phone or computer through a wired or wireless transmission. Moreover, the synchronization timing diagram can provide reference information for waveform analysis for the doctor to make reference.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such a feature may be combined with one or more other features of the other implementations as may be desired and advantageous for any given or particular application.

What is claimed is:

1. An auscultation device, comprising:
an electrocardiogram (ECG) device, configured to receive an ECG signal;
a sound receiver device, configured to receive a heart sound signal, wherein the sound receiver device comprises a microphone;
a synchronization device, configured to transmit a synchronization signal to the ECG device and the sound receiver device, so that the ECG device starts to receive the ECG signal and the sound receiver device starts to receive the heart sound signal in time synchronization, wherein the synchronization device comprises an oscillator; and
a processor, configured to generate an ECG according to the ECG signal, generate a heart sound diagram according to the heart sound signal, and generate a synchronization timing diagram according to the ECG and the heart sound diagram;
wherein the processor calculates a first time difference between an ECG feature point of a first synchronization period and a heart sound diagram feature point of the first synchronization period according to the synchronization timing diagram, and calculates a second time difference between the ECG feature point of a second synchronization period and the heart sound diagram feature point of the second synchronization period;
wherein the processor determines that a measurement result is abnormal when a time gap between the first time difference and the second time difference is greater than a time threshold.

2. The auscultation device of claim 1, further comprising:
a plurality of electrode patches, respectively located on a bottom of the auscultation device; wherein the bottom of the auscultation device is configured to form contact with a skin surface to receive the ECG signal;
wherein the microphone is located at the bottom of the auscultation device and configured to receive the heart sound signal;
wherein, an upper part of the auscultation device is electrically coupled to a lower part of the auscultation device, and the upper part of the auscultation device aligns a mark to select one of a plurality of measurement modes.

3. The auscultation device of claim 1, wherein when the processor determines that the heart sound signal has a noise in a plurality of flat areas, a split sound in a first heart sound, a split sound in a second heart sound, a plurality of heartbeat cycles are irregular or the time difference is greater than the time threshold according to the synchronization timing diagram, the processor determines that the measurement result is abnormal.

4. The auscultation device of claim 3, wherein when the processor determines and analyzes that a split sound exists in the first heart sound or a split sound exists in the second heart sound, the processor further determines a heart sound splitting status by analyzing an inhalation volume and an exhalation volume according to the split sound of the first heart sound and the split sound of the second heart sound, a time difference between the first heart sound and the second heart sound, or whether a noise exists between the first heart sound and the second heart sound.

5. The auscultation device of claim 3, wherein the processor calculates a first cycle time difference between the first heart sound of a first heart sound cycle and the first heart sound of a second heart sound cycle, calculates a second cycle time difference between the first heart sound of the second heart sound cycle and the first heart sound of a third heart sound cycle, calculates a third cycle time difference between the first heart sound of the third heart sound cycle and the first heart sound of a fourth heart sound cycle, an average cycle time difference is calculated based on the first cycle time difference, the second cycle time difference and the third cycle time difference, and subtracts the smallest one from the largest one of the first cycle time difference, the second cycle time difference and the third heart sound time, so as to obtain a first value, and the first value is divided by an average heartbeat to obtain a second value, when the second value is greater than a heartbeat threshold, the processor determines that the heartbeat cycles are irregular.

6. An auscultation method, comprising:
transmitting, via a synchronization device, a synchronization signal to trigger an ECG device to start receiving the ECG signal and trigger a sound receiver device to start receiving a heart sound signal in time synchronization, wherein the sound receiver device comprises a microphone, and the synchronization device comprises an oscillator; and generating an ECG according to the ECG signal, generating a heart sound diagram according to the heart sound signal, and generating a synchronization timing diagram according to the ECG and the heart sound diagram via a processor;

calculating, via the processor, a first time difference between an ECG feature point of a first synchronization period and a heart sound diagram feature point of the first synchronization period according to the synchronization timing diagram, and calculating a second time difference between the ECG feature point of a second synchronization period and the heart sound diagram feature point of the second synchronization period; wherein when a time difference between the first time difference and the second time difference is greater than a time threshold, the processor determines that a measurement result is abnormal.

7. The auscultation method of claim 6, further comprising:

determining that when the heart sound signal has a noise in a plurality of flat areas, a split sound in a first heart sound, a split sound in a second heart sound, a plurality of heartbeat cycles are irregular or the time difference is greater than the time threshold according to the synchronization timing diagram, determining that the measurement result is abnormal.

8. The auscultation method of claim 6, further comprising:

when determining and analyzing that a split sound exists in the first heart sound or a split sound exists in the second heart sound, further determining the heart sound splitting status by analyzing an inhalation volume and an exhalation volume according to the split sound of the first heart sound and the split sound of the second heart sound, a time gap between the first heart sound and the second heart sound, or whether a noise exists between the first heart sound and the second heart sound.

* * * * *